(12) United States Patent
Choi

(10) Patent No.: US 9,645,075 B2
(45) Date of Patent: May 9, 2017

(54) MULTISPECTRAL IMAGER WITH HYBRID DOUBLE LAYER FILTER ARRAY

(71) Applicant: NANOLAMBDA KOREA, Daejeong (KR)

(72) Inventor: Byung Il Choi, Pittsburgh, PA (US)

(73) Assignee: NANOLAMBDA KOREA, Daejeong (KR)

( * ) Notice: Subject to any disclaimer, the term of this patent is extended or adjusted under 35 U.S.C. 154(b) by 0 days.

(21) Appl. No.: 14/553,046

(22) Filed: Nov. 25, 2014

(65) Prior Publication Data
US 2015/0144770 A1    May 28, 2015

Related U.S. Application Data

(60) Provisional application No. 61/908,805, filed on Nov. 26, 2013.

(51) Int. Cl.
| | |
|---|---|
| *B82Y 20/00* | (2011.01) |
| *G01N 21/29* | (2006.01) |
| *H01L 27/146* | (2006.01) |
| *G02B 5/00* | (2006.01) |

(52) U.S. Cl.
CPC ............. *G01N 21/29* (2013.01); *B82Y 20/00* (2013.01); *G02B 5/008* (2013.01); *H01L 27/14621* (2013.01); *H01L 27/14627* (2013.01)

(58) Field of Classification Search
CPC ........ G01N 21/29; B82Y 20/00; G02B 5/008; H01L 27/14621; H01L 27/14627
See application file for complete search history.

(56) References Cited

U.S. PATENT DOCUMENTS

| | | | |
|---|---|---|---|
| 8,816,358 B1 * | 8/2014 | Tsai ...................... | H01L 27/307 257/79 |
| 2004/0151379 A1 * | 8/2004 | Kim ....................... | A61B 5/416 382/209 |
| 2006/0187381 A1 * | 8/2006 | Yokozawa ........ | H01L 27/14621 349/106 |
| 2012/0129269 A1 | 5/2012 | Choi et al. | |

\* cited by examiner

*Primary Examiner* — Tony Ko
(74) *Attorney, Agent, or Firm* — The Marbury Law Group PLLC

(57) ABSTRACT

Hybrid dual layer filter can be employed can be employed as filters. A multispectral imager comprises a two layer filter array monolithically integrated onto detector array, a top layer of pigment based filter and a lower layer of plasmonic nano-optic filter to make a low cost and narrow bandwidth filter without side leaking or side peaks. Multispectral imager comprises a microlens array, a mosaic patterned optical filter array underlying the microlens array and including a two-dimensional repetition of a unit mosaic pattern, and a pixelated detector array underlying the mosaic patterned optical filter array. The unit mosaic pattern comprises an array of composite filter elements having different peaks in a respective transmittance spectrum. Each composite filter element comprises a pigment based filter portion and a plasmonic nano-optic filter portion.

18 Claims, 10 Drawing Sheets

500

501

502

503

MULTISPECTRAL IMAGER WITH HYBRID DOUBLE LAYER FILTER ARRAY

BACKGROUND

Demand for a low-cost snapshot multi spectral imager has been increasing for various applications, which include accurate color reproduction, machine/robot vision, plant and vegetation research, food processing, counterfeit detection, early stage diagnosis of cancer, medical in-vivo imaging, and defense applications (point/stand-off optical spectral detection systems for remote sensing). Especially, accurate color reproduction is highly desired for a growing number of smart displays equipped with color camera modules and color displays.

A typical multispectral imager essentially consists of either rotating filter wheels, mechanically diced thin-film dichroic filters mounted in front of an image sensor, or multiple cameras with bulk dichroic filters. Even for those touted as commercial systems, there is no real volume production pathway with significant price or reduced complexity enhancements for as few as tens or hundreds of units.

There is a low cost color filter array used for typical CCD or CMOS image sensor which is a negative type photosensitive material that can be patterned with UV light. It consists of pigments to define the spectrum of the color filter, a dispersant polymer for pigment dispersion, an initiator to generate the radical for the polymerization reaction, a monomer to be polymerized and an alkaline soluble polymer to control the development property. The photo-polymerization starts with the radicals generated when the initiator is exposed to UV light. When the radical gets in contact with the monomers, the polymerization starts and forms the high molecular weight polymer insoluble for the developer. The un-exposure area is not polymerized and is removed during the development process. As a result, the pattern profile is formed. This type of color filter array requires coating, pre-bake, exposure, development, rinse and post-bake multiple times to make a mosaic pattern. Although this type of filter can be made at low cost for one filter, the cost increases as number of filter type of an array increases. Also the bandwidth is broad and the band selectivity is limited to a visual range.

Recently, it has been found that certain nanostructures work as an optical filter, and has a strong advantage compared to prior technologies. Multiple, or almost infinite number of, optical filters can be made on a single layer, at no additional cost. The spectral shapes of these plasmonic nano-optical filters can be controlled. It can be narrowed but usually at an expense of the transmission power. Also usually unwanted second peaks or third peaks are generated at relatively high transmission power. For the above reasons, low cost and clean spectral filters are not readily available for multi-spectral imager application so far.

SUMMARY OF THE INVENTION

Hybrid dual layer filter can be employed can be employed as filters. A multispectral imager comprises a two layer filter array monolithically integrated onto detector array, a top layer of pigment based filter and a lower layer of plasmonic nano-optic filter to make a low cost and narrow bandwidth filter without side leaking or side peaks.

DETAILED DESCRIPTION OF THE PREFERRED EMBODIMENTS

Unless otherwise specified, the words "a" or "an" as used herein mean "one or more". The term "light" includes visible light as well as UV and IR radiation. The invention includes the following embodiments.

Figure 1:
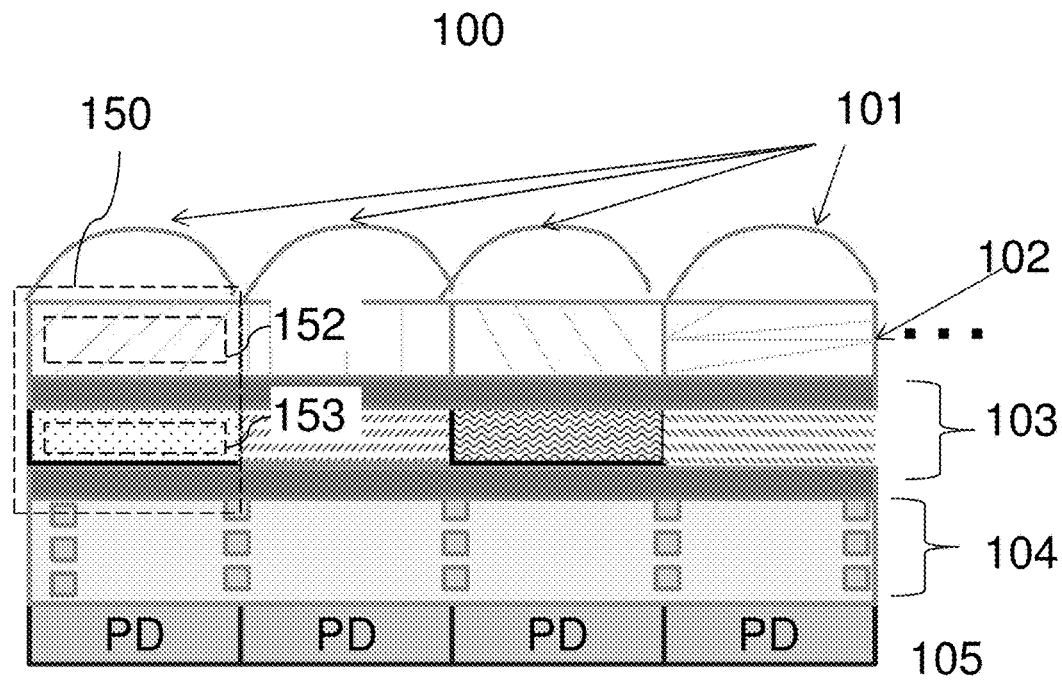
FIG. 1 is a schematic representation in a vertical cross-sectional view of a FSI (front side illumination) multispectral imager with dual layer filter arrays according to an embodiment of the present disclosure.

Referring to FIG. 1, a vertical cross-sectional view of a first exemplary multispectral imager 100 is shown, which can be employed to generate accurate-color, multispectral, and/or 3D images. The first exemplary multispectral imager 100 contains a microlens array 101, a pigment based color filter array 102, a plasmonic nanofilter array 103, at least one metal interconnection layer 104, and a pixelated photo detector array 105. The number of different band pass filters for the mosaic pattern can be more than four. The vertical cross-sectional view of FIG. 1 represents a front side illumination sensor structure.

As used herein, a plasmonic filter refers to a patterned metal film with subwavelength-size periodic hole arrays. A plasmonic filter acts as an optical filter due to the interference of surface plasmon polaritons (SPP) between adjacent holes. A plasmonic nanofilter refers to a plasmonic filter having patterned shapes of which at least one dimension is a nanoscale dimension (less than 1 micron).

Figure 2:
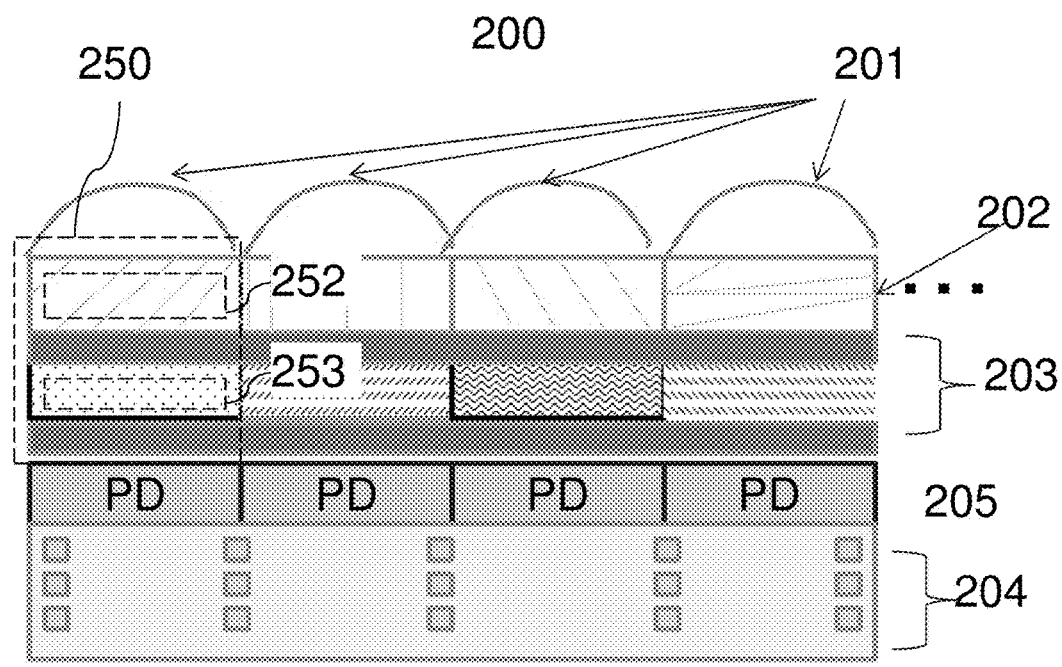
FIG. 2 is a schematic representation in a vertical cross-sectional view of a BSI (back side illumination) multispectral imager with dual layer filter arrays according to an embodiment of the present disclosure.

Referring to FIG. 2, a vertical cross-sectional view of a second exemplary multispectral imager 200 is shown, which can be employed to generate accurate-color, multispectral, and/or 3D images. The second exemplary multispectral imager 200 contains a microlens array 201, a pigment based color filter array 202, and a plasmonic nanofilter array 203, at least one metal interconnection layer 204, and pixelated photo detector array 205. The number of different band pass filters for the mosaic pattern can be more than four. The vertical cross-sectional view of FIG. 1 represents a back side illumination sensor structure.

Figure 3A:
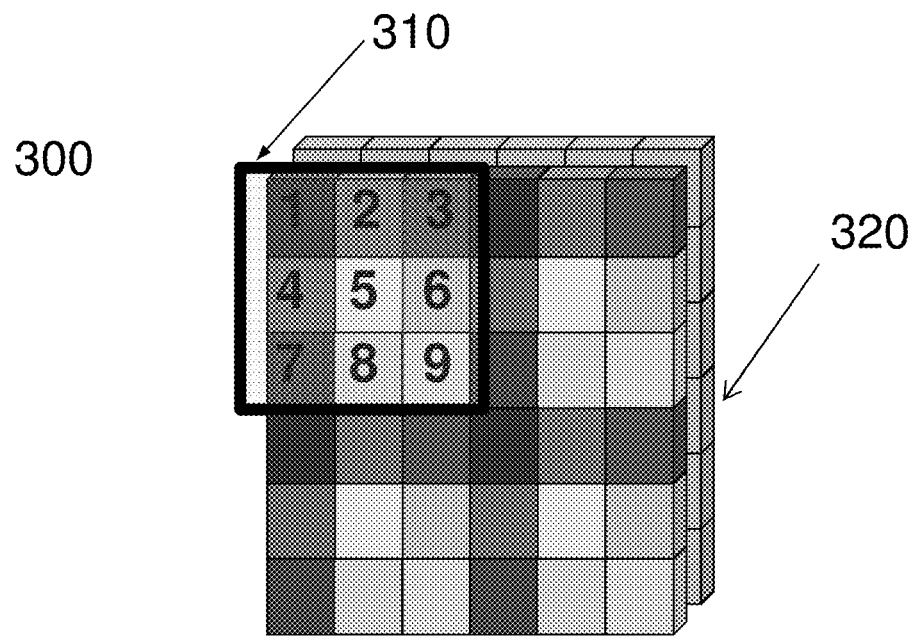
FIG. 3A is a schematic representation in a perspective view of a multispectral imager with monolithically integrated multispectral filter array with a mosaic pattern.

Referring to FIG. 3A, an example of multispectral imager 300 is shown, including a filter array mosaic pattern 310 of multispectral imager, and a detector 320 with associated pixel array. The filters may be made of a layer or layers of highly conductive structured materials. The highly conductive structured material layer may include a periodic pattern or patterns of elements. The elements can have shapes and sizes configured such that a transmittance spectrum of the conductive layer has at least one pass band within the target wavelength range.

Figure 3B:
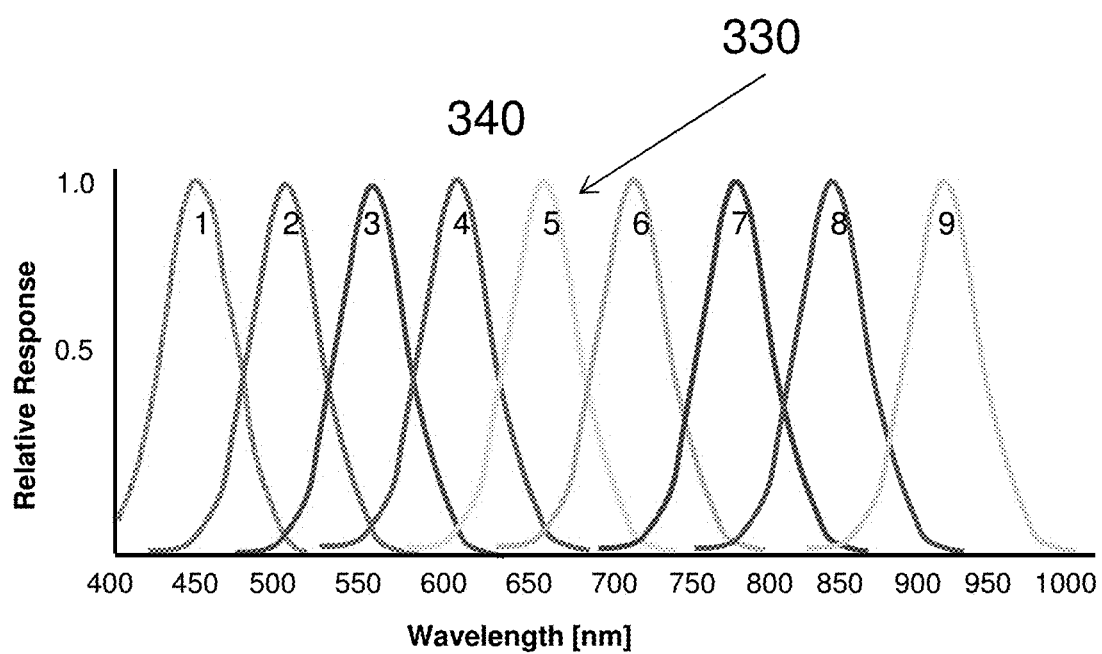
FIG. 3B is a schematic representation of a spectral response of a multispectral filter array.

FIG. 3B illustrates a schematic representation of a spectral response of an ideal multispectral filter array.

Figure 4A:
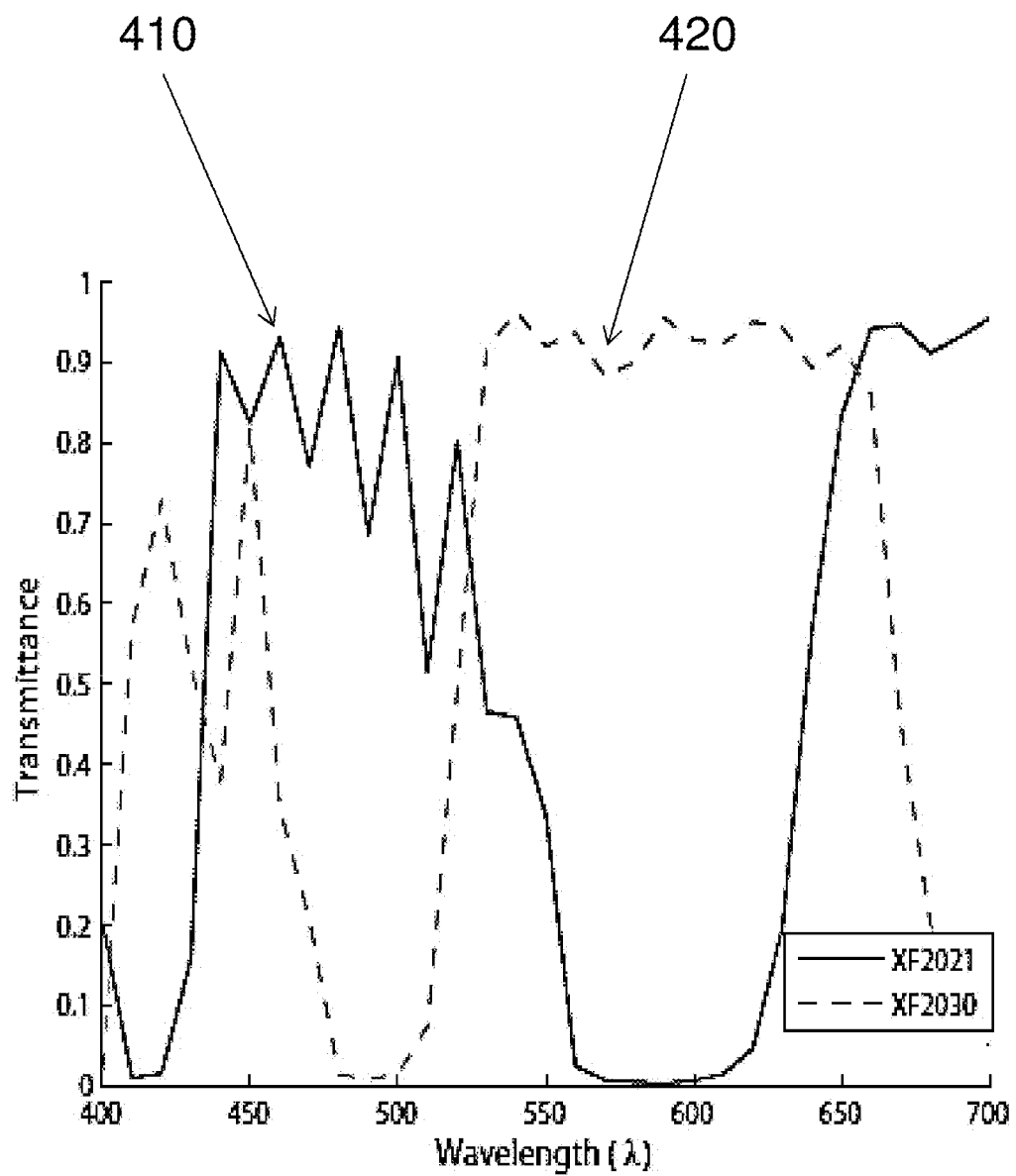
FIGS. 4A, 4B and 4C show spectral responses of different types of multispectral band pass filters for multispectral image.
Figure 4B:
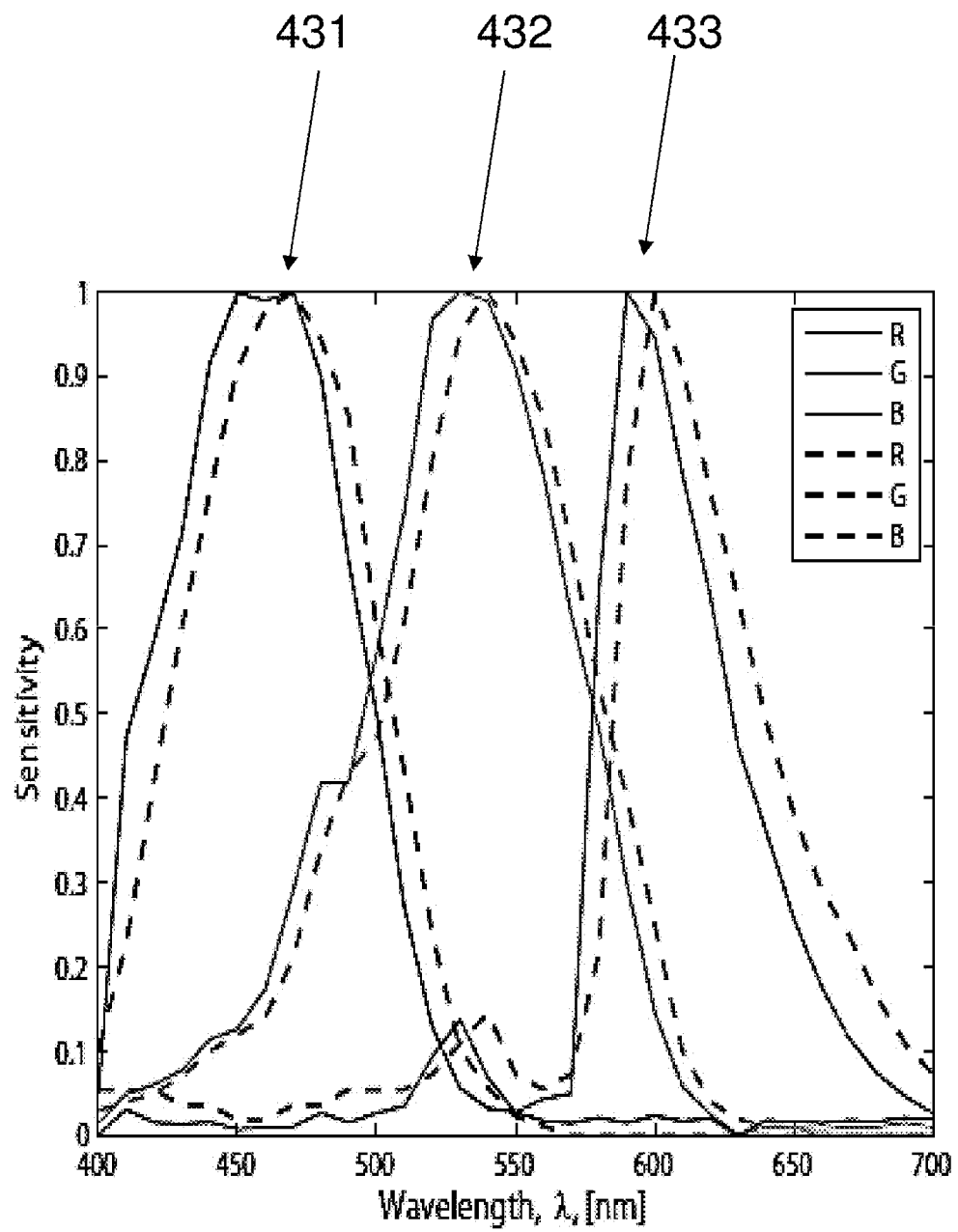
Figure 4C:
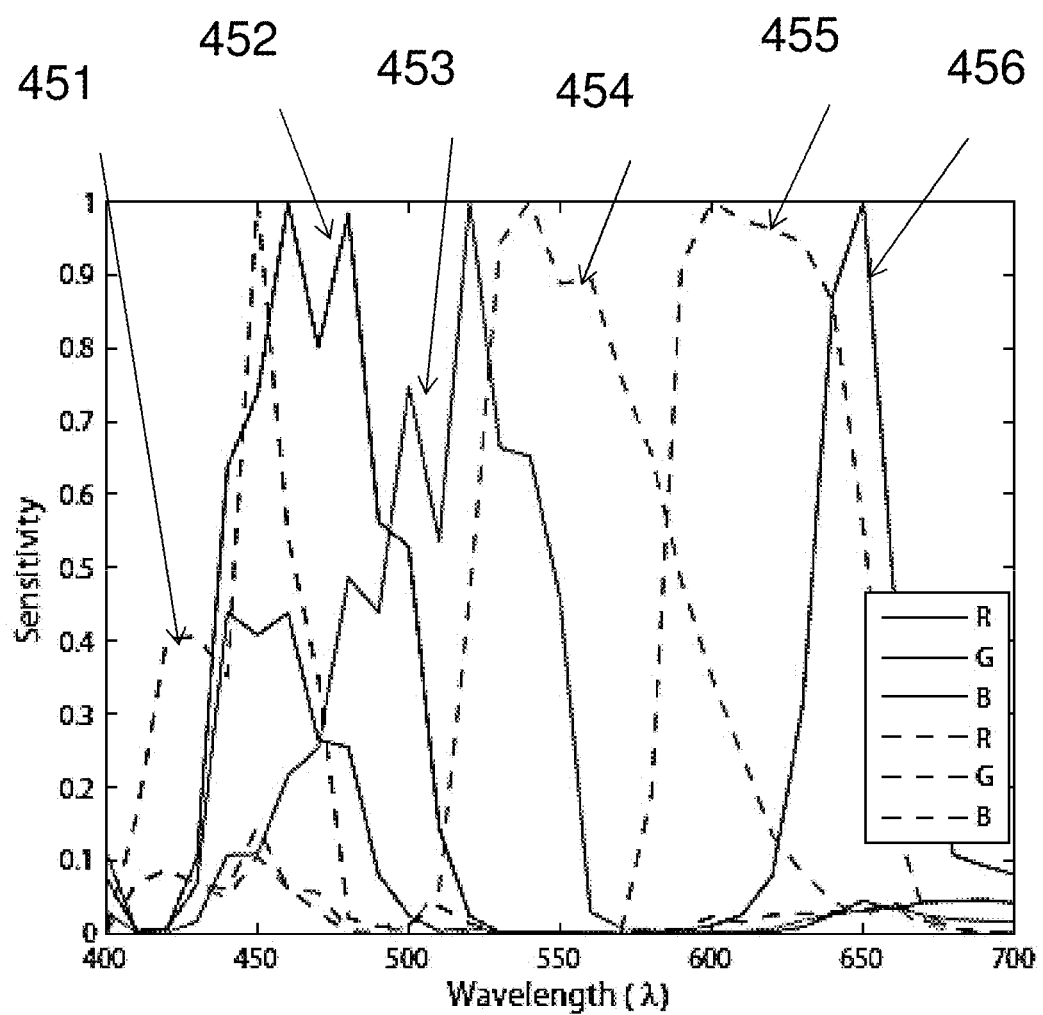

Referring to FIGS. 4A, 4B and 4C, examples of spectral responses of different types of dichroic filters are shown. The respective pass wavelength ranges (410, 420, 431, 432, 433, 451, 453, 453, 454, 455, 456) are illustrated for each dichroic filters. Some of the dichroic filters show second peaks or second bands. A dichroic filter is an interference-based color filter that selectively passes light within a small wavelength range (a pass band) while reflecting light outside of the selective pass band.

Figure 5A:
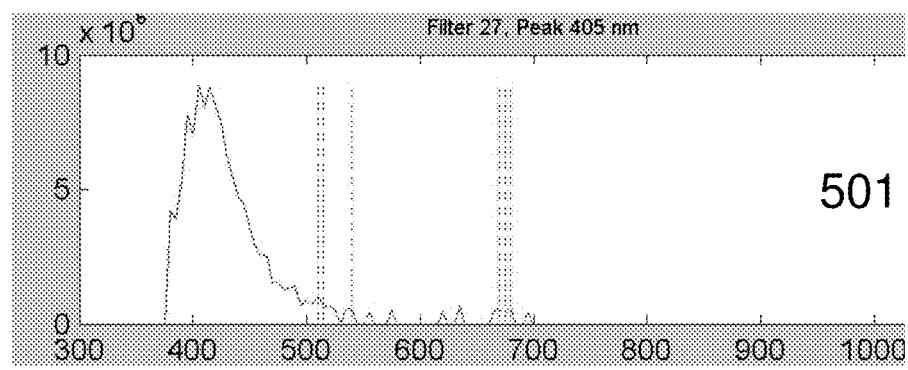
FIGS. 5A, 5B, and 5C show examples of spectral responses of plasmonic nanofilters.
Figure 5A:
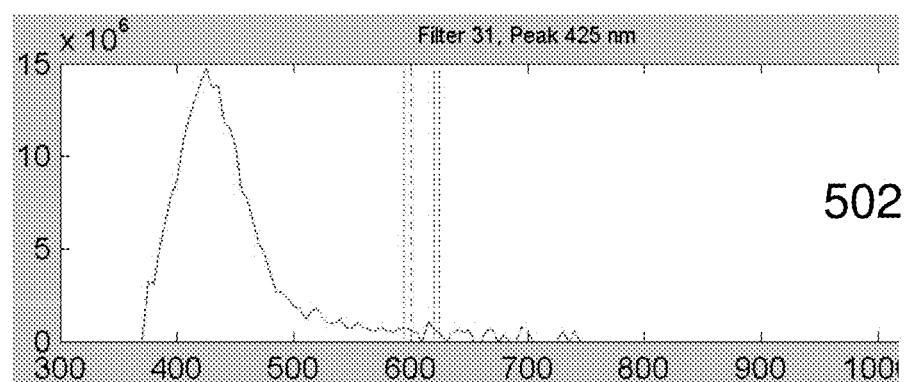
Figure 5A:
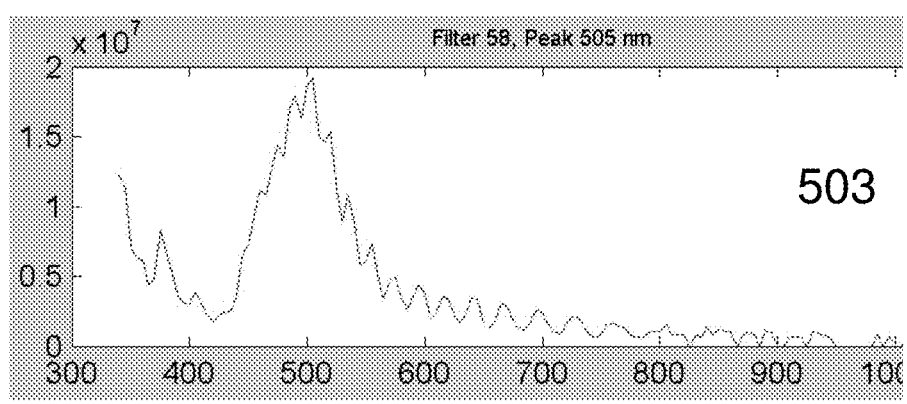
Figure 5B:
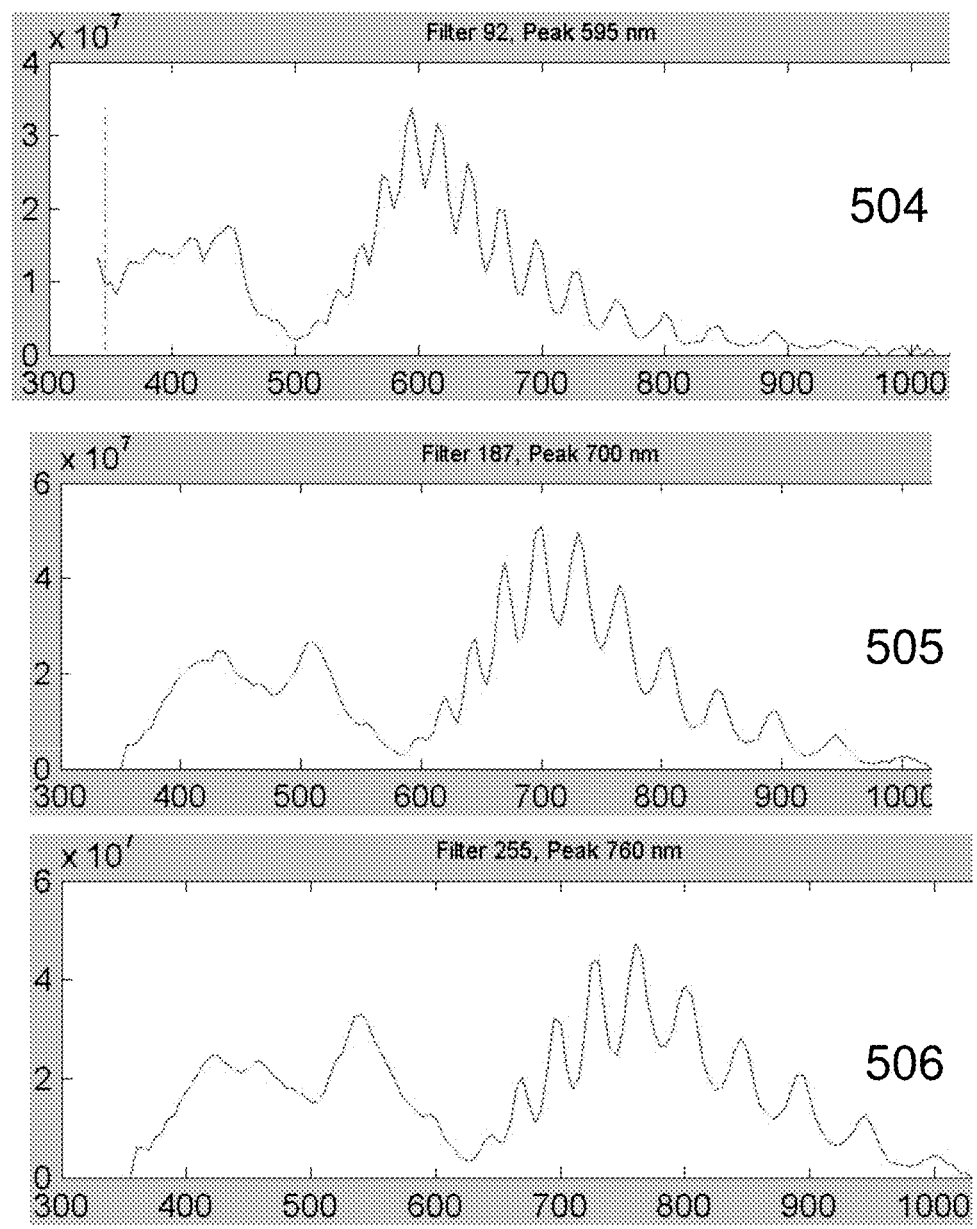
Figure 5C:
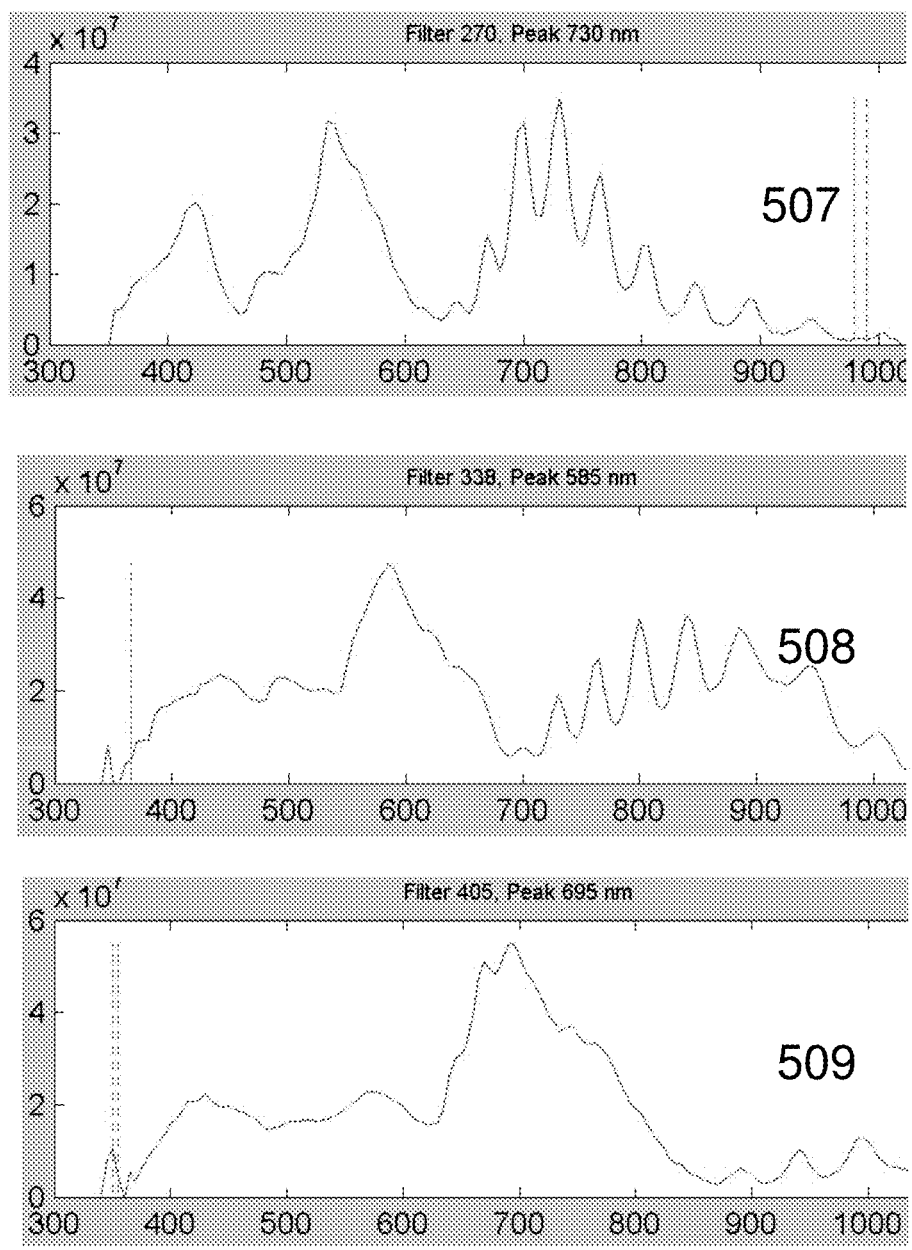

Referring to FIGS. 5A, 5B and 5C, examples of spectral responses of different wavelength plasmonic nano-optic filters in the visible and near infrared range 501, 502, 503, 504, 505, 506, 507, 508, and 509 are shown. The filters may be made of a layer, or layers, of highly conductive structured materials. The highly conductive structured material layer(s) may include a periodic pattern, or patterns, of elements. The periodic pattern(s) of elements can have shapes and sizes that are configured such that a transmittance spectrum of the conductive layer has at least one pass band within the target wavelength range. The filters can show broad bandwidths and second and third peaks that are located outside the range of the first peak, i.e., outside the wavelength range within which transmission of light is desired for a given filter.

Figure 6A:
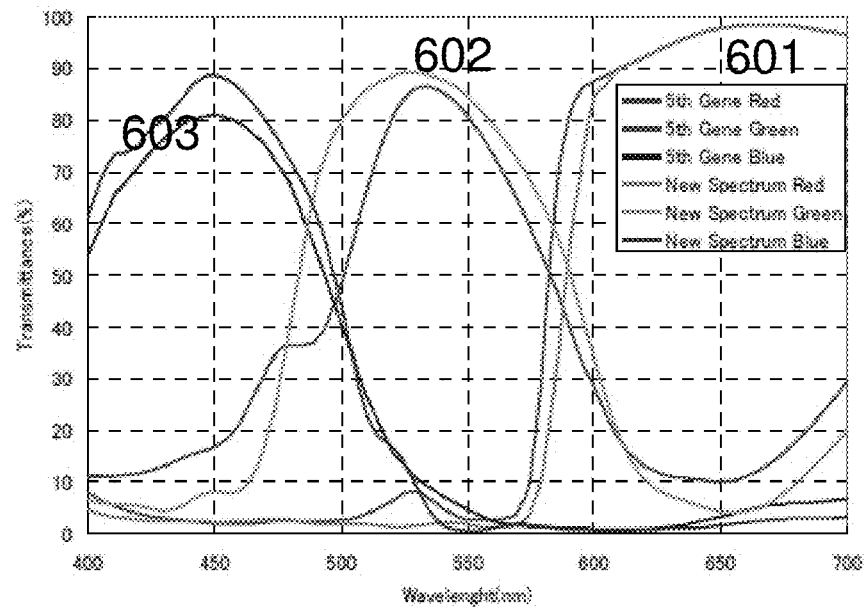
FIGS. 6A and 6B show examples of spectral responses of pigment based RGB CMY filters.
Figure 6B:
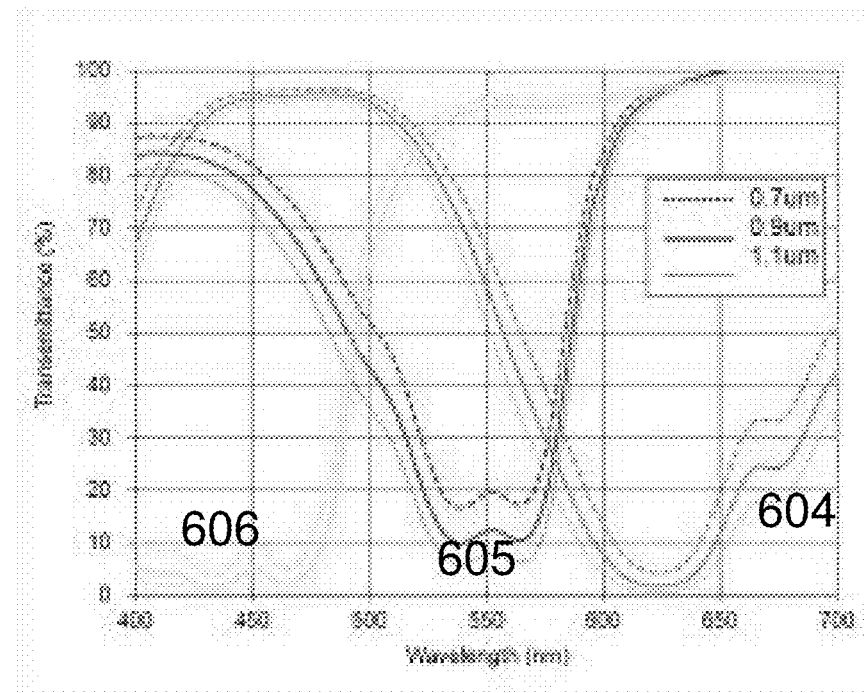

Referring to FIGS. 6A and 6B, examples of different peak-wavelength pigment based filters in the visible range 601, 602, 603, 604, 605, and 606 are shown. The filters show broad bandwidths and leakage in the longer wavelength ranges.

Figure 7A:
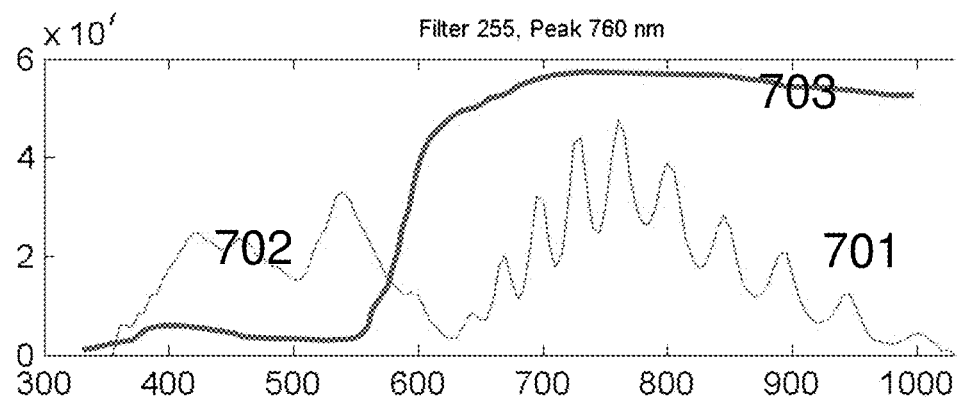
FIG. 7A shows a schematic representation of an overlay of spectral responses of a plasmonic nanofilter with pigment based RED color filter.

Referring to FIG. 7A, a spectral response (701, 702) of a plasmonic nanofilter is overlaid with a spectral response 703 of a pigment based RED color filter.

Figure 7B:
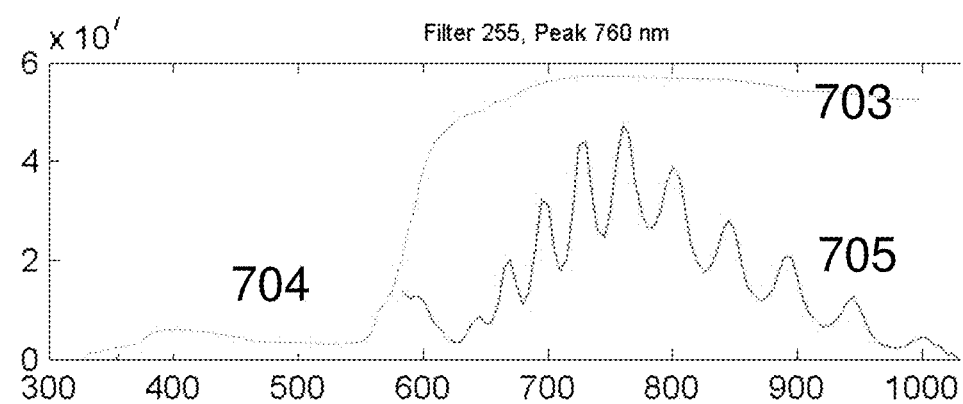
FIG. 7B shows a schematic representation of the resulting of spectral response of a dual layer filter made of a plasmonic nanofilter and pigment based RED color filter.

Referring to FIG. 7B, the spectral response (704, 705) of a dual layer filter made of a plasmonic nanofilter and pigment based RED color filter is shown. The transmission spectra of the dual layer filter can be obtained by multiplying the transmittance spectra of the plasmonic nanofilter with the transmittance spectra of the respective pigment based filter within the same dual layer filter.

According to an aspect of the present disclosure, a multispectral imager is provided. The multispectral imager comprises a microlens array (101 or 201), a mosaic patterned optical filter array {(102, 103) or (202, 203)} underlying the microlens array and including a two-dimensional repetition of a unit mosaic pattern 310, and a pixelated detector array (105 or 205) underlying the mosaic patterned optical filter array {(102, 103) or (202, 203)}. The unit mosaic pattern comprises an array of composite filter elements (150 or 250) having different peaks in a respective transmittance spectrum. Each composite filter element (150 or 250) comprises a pigment based filter portion (152 or 252) and a plasmonic nano-optic filter portion (153 or 253).

In one embodiment, the unit mosaic pattern 310 can be an m×n rectangular pattern, wherein m and n are independent integers greater than 1. In one embodiment, the unit mosaic pattern can comprise a combination of multiple hexagonal patterns that can be repeated in two directions.

In one embodiment, each plasmonic nano-optic filter portion (153 or 253) can comprise a conductive material layer including a periodic pattern of geometric shapes. In one embodiment, the plasmonic nano-optic filter portions (153, 253) within the unit mosaic pattern can comprise the same conductive material having different periodic patterns of geometrical shapes. In one embodiment, the conductive material can be an elemental metal or an intermetallic alloy of at least two elemental metals. In one embodiment, shapes and sizes of the geometrical shapes can be configured such that a transmittance spectrum of each second layer has at least one pass band within a respective pass band of the first layer within a same composite filter element.

In one embodiment, the multispectral imager can be configured to generate a multispectral image employing the mosaic patterned optical filter array. In one embodiment, each pigment based filter portion (152, 252) in the unit mosaic pattern can have a different composition from other pigment based filter portions (152, 252) in the unit mosaic pattern.

In one embodiment, the transmission spectra of each composite filter element (150 or 253) can be the same as the product of a respective pigment based filter portion (152 or 252) in the composite filter element (150 or 250) and a respective plasmonic nano-optic filters (153 or 253) in the composite filter element (150 or 250).

In one embodiment, at least one metal interconnect layer 104 can overlie the pixelated detector array 105. In another embodiment, at least one metal interconnect layer 204 can underlie the pixelated detector array 204.

In one embodiment, each pigment based filter portion (152 or 252) can overlie a respective plasmonic nano-optic filter portion (153, 163) within each composite filter element (150 or 250). In one embodiment, each composite filter element (150, 250) may comprise a portion of an optional upper transparent material layer overlying a respective plasmonic nano-optic filter portion (153 or 253), and a portion of an optional lower transparent material layer underlying the respective plasmonic nano-optic filter portion (153 or 253). In one embodiment, the pixelated detector array (104, 204) can comprise semiconductor photodetectors.

In one embodiment, a method of interpreting bio-chemical contents of an organism is provided. The multispectral imager of the present disclosure can be provided. A multi-spectral image of an organism can be taken. Health condition of the organism can be identified by correlating the multispectral image with spectral distribution data from organisms with previously characterized health conditions. In one embodiment, the organism can be a human, and the multispectral image can be taken from a part of a human body.

In one embodiment, a method of acquire a multispectral image is provided. The spectral imager of the present disclosure can be provided. A multispectral image can be taken employing the spectral imager.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention. All of the publications, patent applications and patents cited in this specification are incorporated herein by reference in their entirety.

What is claimed is:

1. A multispectral imager comprising:
   a microlens array;
   a mosaic patterned optical filter array underlying the microlens array and including a two-dimensional repetition of a unit mosaic pattern; and a pixelated detector array underlying the mosaic patterned optical filter array, wherein the pixelated detector array comprises semiconductor photodetectors, wherein:

the multispectral imager is configured to concurrently generate N distinct spectral images of an object during operation such that the N distinct spectral images correspond to light emission from the object within N distinct spectral pass bands, wherein N is an integer greater than 3;

the unit mosaic pattern comprises an array of N composite filter elements having different peaks in a respective transmittance spectrum, wherein each peak corresponds to a center of a respective one of the N distinct spectral pass bands, and at least one of the N distinct spectral pass bands includes a pass band centered within an infrared wavelength range;

each composite filter element comprises a pigment based filter portion and a plasmonic nano-optic filter portion that underlies the pigment based filter portion; and each plasmonic nano-optic filter portion comprises a respective patterned metal film with a respective subwavelength-size periodic hole array therein, and instances of a hole having a geometrical shape are repeated as a two-dimensional array within each subwavelength-sized periodic hole array, and adjacent instances of holes provide interference of surface plasmon polaritons therebetween to provide a respective transmittance spectrum within each subwavelength-sized periodic hole array, and the geometrical shape of the hole has at least one dimension that is less than 1 micron within each subwavelength-sized periodic hole array.

2. The multispectral imager of claim 1, wherein said unit mosaic pattern is an m×n rectangular pattern, wherein m and n are independent integers greater than 1.

3. The multispectral imager of claim 1, wherein said unit mosaic pattern comprises a combination of multiple hexagonal patterns.

4. The multispectral imager of claim 1, wherein each plasmonic nano-optic filter comprises a conductive material layer including a periodic pattern of geometric shapes.

5. The multispectral imager of claim 1, wherein the plasmonic nano-optic filter portions within the unit mosaic pattern comprise a same conductive material having different periodic patterns of geometrical shapes.

6. The multispectral imager of claim 5, wherein the conductive material is an elemental metal or an intermetallic alloy of at least two elemental metals.

7. The multispectral imager of claim 5, wherein shapes and sizes of the geometrical shapes are configured such that a transmittance spectrum of each plasmonic nano-optic filter portion has at least one pass band within a pass band of the respective pigment based filter portion within a same composite filter element.

8. The multispectral imager of claim 1, the multispectral imager is configured to generate a multispectral image employing said mosaic patterned optical filter array.

9. The multispectral imager of claim 1, wherein each pigment based filter portion in the unit mosaic pattern has a different composition from other pigment based filter portions in the unit mosaic pattern.

10. The multispectral imager of claim 1, a transmission spectra of each composite filter element is the same as the product of a transmission spectra of a respective pigment based filter portion in the composite filter element and a transmission spectra of a respective plasmonic nano-optic filter portion in the composite filter element.

11. The multispectral imager of claim 1, further comprising at least one metal interconnect layer overlying the pixelated detector array.

12. The multispectral imager of claim 1, further comprising at least one metal interconnect layer underlying the pixelated detector array.

13. The multispectral imager of claim 1, wherein each pigment based filter portion overlies a respective plasmonic nano-optic filter portion within each composite filter element.

14. The multispectral imager of claim 1, wherein each composite filter element comprises:

a portion of an upper transparent material layer overlying a respective plasmonic nano-optic filter portion; and a portion of a lower transparent material layer underlying the respective plasmonic nano-optic filter portion.

15. A method of interpreting bio-chemical contents of an organism, comprising:

providing the multispectral imager of claim 1;

taking a multispectral image of an organism; and identifying health condition of the organism by correlating the multispectral image with spectral distribution data from organisms with previously characterized health conditions.

16. The method of claim 15, wherein the organism is a human, and the multispectral image is taken from a part of a human body.

17. A method of acquire a multispectral image, comprising:

providing the spectral imager of claim 1; and taking a multispectral image employing the spectral imager.

18. The multispectral imager of claim 1, wherein each plasmonic nano-optic filter portion within the unit mosaic pattern comprises a same conductive material layer that extends across an entirety of the unit mosaic pattern and including a same number of subwavelength-size periodic hole arrays a total number of composite filter elements in the unit mosaic pattern, wherein each of the subwavelength-size periodic hole arrays has different geometrical shapes for holes therein.

* * * * *